US008609381B2

(12) United States Patent
de Sa et al.

(10) Patent No.: US 8,609,381 B2
(45) Date of Patent: Dec. 17, 2013

(54) METHODS TO CONTROL BACTERIAL GROWTH IN FERMENTATION PROCESSES

(75) Inventors: José Sebastião de Sa, Sao Bernardo do Campo (BR); Abel Oliveira, Sao Paulo (BR)

(73) Assignee: Dow Brasil Sudeste Industrial Ltda., Sao Paulo (BR)

( * ) Notice: Subject to any disclaimer, the term of this patent is extended or adjusted under 35 U.S.C. 154(b) by 388 days.

(21) Appl. No.: 12/666,837

(22) PCT Filed: Jun. 26, 2008
(Under 37 CFR 1.47)

(86) PCT No.: PCT/IB2008/001683
§ 371 (c)(1),
(2), (4) Date: Jun. 30, 2010

(87) PCT Pub. No.: WO2009/001205
PCT Pub. Date: Dec. 31, 2008

(65) Prior Publication Data
US 2010/0297719 A1    Nov. 25, 2010

Related U.S. Application Data

(60) Provisional application No. 60/937,476, filed on Jun. 28, 2007.

(51) Int. Cl.
*C12P 7/06* (2006.01)

(52) U.S. Cl.
USPC .......................................................... 435/161

(58) Field of Classification Search
None
See application file for complete search history.

(56) References Cited

U.S. PATENT DOCUMENTS

| 5,888,788 | A | 3/1999 | De Miniac |
| 6,187,963 | B1 | 2/2001 | Etzkorn et al. |
| 2011/0027846 | A1 | 2/2011 | De Sa et al. |

FOREIGN PATENT DOCUMENTS

| BR | 9104225 | 12/1991 |
| BR | 9203990 | 4/1994 |
| CA | 1102725 | 6/1981 |
| EP | 217339 | 4/1987 |
| GB | 1553662 | 10/1979 |
| GB | 2189146 | 4/1987 |
| WO | 9955439 | 11/1999 |
| WO | 0123534 | 4/2001 |
| WO | 0205642 | 1/2002 |

OTHER PUBLICATIONS

Essia Ngang et al., "Alcoholic fermentation of beet molasses: effects of lactic acid on yeast fermentation parameters", Applied Microbiology and Biotechnology, 1989, vol. 31, pp. 125-128.*
Alcarde et al., "Influence of gamma radiation on microbiological parameters of the ethanolic fermentation of sugar-cane must", Radiation Physics and Chemistry, 2003, vol. 66, pp. 411-413, Elsevier Science Ltd.
Aquarone et al., "Chloramphenicol Used as a Disinfectant in the Alcohol Fermentation of Sugar Cane Molasses", Anais de Farmacia e Quimica de Sao Paulo, 1960, vol. 11 No. 3/4, pp. 49-60.
Aquarone, "Penicillin and Tetracycline as Contamination Control Agents in Alcoholic Fermentation of Sugar Cane Molasses", Contamination Control Agents in Alcoholic Fermentation, Applied Microbiology, 1960, vol. 8, pp. 263-268.
De Oliva-Neto et al., "Susceptibility of *Saccharomyces cerevisiae* and lactic acid bacteria from the alcohol industry to several antimicrobial compounds", Brazilian Journal of Microbiology, 2001, vol. 32 No. 1, pp. 10-14.
Gorman et al., "A Review Antimicrobial activity, uses and mechanism of action of glutaraldehyde", The Journal of Applied Bacteriology, 1980, vol. 48 No. 2, pp. 161-190, The Society for Applied Bacteriology.
Hynes et al., "Use of virginiamycin to control the growth of lactic acid bacteria during alcohol fermentation", Journal of Industrial Microbiology and Biotechnology, 1997, vol. 18 No. 4, pp. 284-291, Society for Industrial Microbiology.
Islam et al., "Stability of virginiamycin and penicillin during alcohol fermentation", Biomass and Bioenergy, 1999, vol. 17 No. 5, pp. 369-376, Elsevier Science Ltd.
Serra et al., "Biological Control of Alcohol Fermentation under Industrial Conditions", Proc. Int. Symp. Alcohol Fuels Technol., 4th, 1981, pp. 67-70.
"Dow Antimicrobial 7287" http://www.dow.com/biocides/prod/anti7287.htm>, 2008.
"UCARCIDE 250 Antimicrobial" http://www.dow.com/biocides/prod/ucar250a.htm>, 2008.

* cited by examiner

*Primary Examiner* — Suzanne M Noakes
(74) *Attorney, Agent, or Firm* — Tifani M. Edwards

(57) ABSTRACT

A method of producing a fermentation-based product, such as ethanol, comprises fermenting a sugar-containing medium with yeast in the presence of an aliphatic or aromatic monoaldehyde or dialdehyde, a formaldehyde-releasing compound, or a combination thereof, in an amount sufficient to reduce or control a bacterial population in the sugar-containing medium. The additive may enable reduction or elimination of antibiotics for this purpose, while showing reductions in percent infection, process variability and interference with yeast viability.

5 Claims, No Drawings

METHODS TO CONTROL BACTERIAL GROWTH IN FERMENTATION PROCESSES

CROSS REFERENCE TO RELATED APPLICATIONS

This is a §371 application of PCT International Patent Application Number PCT/IB2008/001683 filed Jun. 26, 2008, and claims priority from provisional application Ser. No. 60/937,476 filed Jun. 28, 2007, each of which is incorporated herein by reference in its entirety.

BACKGROUND OF THE INVENTION

1. Technical Field

This invention relates to the field of fermentation processes. More particularly, it relates to methods and means for controlling bacteria in fermentation processes for producing ethanol.

2. Background of the Art

A commonly-employed method of producing ethanol involves fermentation based on yeast. This process consists basically of the following operations: (a) molasses handling, dilution, clarification and heat treatment, (b) anaerobic fermentation by a selected yeast strain, previously grown under controlled conditions, (c) yeast separation from the broth, and (d) alcohol separation by distillation and eventual storage. For detailed descriptions and technical details, see, for example: Harrison, J. S. and Graham, J. C. J., "Yeast in Distillery Practice" in A. H. Rose and J. S. Harrison (Eds.) "The Yeasts" 3 (6) 283-348 (1970), Academic Press; Kampen, W. H., Sugar y Azucar 70 (8) 36-39, 42-43 (1975); and L'Anson, J. A. P., Process Biochem. 11 (7) 35-39 (1971). Many processing operations begin with the juice or syrup which has been extracted from a solid fiber matrix of a sugar source selected from, for example, sugar cane, corn, or sugar beets, while others begin with direct fermentation of the sugar source which has been comminuted into fragments or highly pulverized. Such methods represent generally efficient ways to produce a variety of alcohols, and in particular ethanol, from a selected fermentation substrate.

However, a problem is encountered when bacteria contaminate the fermentation substrate. The bacteria, when present at relatively high levels, compete with the yeast and may reduce the fermentative yield. Furthermore, the bacteria may cause flocculation, requiring additional measures to obtain ethanol therefrom. Those skilled in the art have developed various means of addressing the bacteria problem. The most commonly used method at present involves adding biocides to the substrate. Examples of these biocides include quaternary ammonium compounds, carbamates, and halogenated phenols. Alternatively or in combination with biocides, hydrogen peroxide may be used or antibiotics may be used. Such may include, for example, an antibiotic known as KAMORAN HJ™, which is defined as 4-[2-[5-ethyl-5-[5-[6-hydroxy-6-(hydroxymethyl)-3,5-dimethyl-oxan-2-yl]-3-methyl-oxolan-2-yl]oxolan-2-yl]-9-hydroxy-2,8-dimethyl-1,6-dioxaspiro-[4.5]dec-7-yl]-3-methoxy-2-methyl-pentanoate.

Unfortunately, some biocides and antibiotics may undesirably contaminate the ethanol, cause flocculation, or generally require a post-treatment or additional processing of the fermentation medium and/or the alcohol product. Such post-treatments or additional processing may add to the time, cost, and/or convenience of producing the ethanol. Biocides and antibiotics may also reduce yeast level during the process, which is undesirable.

In view of the above, it would be desirable in the art to find methods and means for preparing ethanol via fermentation processes that eliminate or reduce these problems and/or the need for biocides and antibiotics conventionally used for such processes.

SUMMARY OF THE INVENTION

Accordingly, the present invention provides, in one aspect, a method of producing fermentation-based products comprising fermenting a sugar-containing medium with yeast in the presence of an additive selected from the group consisting of aliphatic and aromatic monoaldehydes and dialdehydes; non-halogenated phenolics and their corresponding sodium and potassium salts; compounds that release formaldehyde upon contact with water; guanidine-based compounds; isothiazolinone compounds; 2-bromo-2-nitro-1,3-propanediol ("Bronopol"); bromonitrostyrene; 2,2-dibromo-3-nitrilopropionamide (DBNPA); 2,6-dimethyl-m-dioxan-4-ol acetate; and combinations thereof; in an amount sufficient to reduce or control a bacterial population in the sugar-containing medium.

In another aspect, the present invention provides a method wherein the fermentation-based product is specified as ethanol.

In yet another aspect, the invention provides a method of producing ethanol comprising fermenting a sugar-containing medium with yeast in the presence of glutaraldehyde, in an amount sufficient to reduce or control a bacterial population in the sugar-containing medium.

DETAILED DESCRIPTION OF THE INVENTION

The present invention is a method for carrying out ethanol production from a variety of sugar-containing sources, including, but not limited to, sugar cane, corn, sugar beets, cellulosic feedstocks, date palm, sorghum, sugar maple, combinations thereof, and the like. "Sugar," as used herein, refers to any chemically-defined sugar, i.e., a monosaccharide, disaccharide, trisaccharide, or oligosaccharide, that is suitable to be fermented to produce a fermentation product, in particular, ethanol. Preparation of the sugar-containing medium used for fermentation is well known to those skilled in the art, and generally includes either extraction of a juice via crushing of the sugar-containing source and/or of its seeds. Recovery of sucrose from the cane plant requires the separation of juice from the fibrous material in the structure of the stalk. The tissue inside the rind of the stalk is a matrix of thin-walled parenchyma storage cells in which vascular bundles are imbedded. This parenchymatous tissue is called the "pith," while the rind and the vascular bundles are collectively referred to as the "fiber." Sucrose is present principally in the parenchyma storage cells. These cells are easily ruptured, and the most commonly employed methods to extract the juice are milling or crushing, called grinding; hot water extraction, or "diffusion"; or a combination of both methods. During grinding, hot water is sprayed over the shredded material to extract any remaining sugar and add it to the raw juice. In the diffusion method, the cane is prepared by a combination of knife mills and roller crushers. The solid waste remaining after extraction of the sugar is known as pulp or sugar cane bagasse, which is separated out and dried for use as fuel.

The raw juice is then heated and spun in a centrifuge, whereby a thick syrup is forced out through small holes in the centrifuge walls. This syrup is called molasses, which has its own uses, such as in commercial table syrup or animal feed.

The remaining material, a solid, is then sent to a refinery. Here it is redissolved and decolorized, and may then be either recrystallized into a desired size, or used to prepare a fermentation substrate, as in the case in the present invention.

In the case of some materials, such as sugar cane and cellulosic feedstocks, additional pre-fermentation steps may be required, such as enzyme or acid cleavage to break glycosidic bonds, and the like. Similar methods are typically used for extraction and preparation of sugar from the other sugar-containing sources, but those skilled in the art will understand that any method may be employed in the practice of the invention, provided that the result is a sugar-containing source in a form that is useful for preparation of a sugar-containing medium for fermentation, i.e., a fermentation substrate, which is an aqueous suspension of the sugar. The amount of water is desirably based upon the amount of sugar, as is well known to those skilled in the art. In general, too much water may be undesirable because it will dilute the final ethanol concentration, hence increasing the energy demand for purification, while too little water will not produce an adequate suspension.

In addition to the sugar and water, the fermentation substrate will include yeast. The particular yeast inoculum employed in the practice of the present invention is not considered to be critical. Illustrative yeast strains useful in the practice of the invention are those maintained at, for example, the Central American Research Institute for Industry, Avenida La Reforma 4-47, Zone 10, Guatamala, C.A. (Instituto Centroamericano de Investigacion y Tecnologia Industrial, "ICAITI") as strains *Saccharomyces cerevisae* L-180; *Saccharomyces cerevisae* L-181; *Saccharomyces* L-200; *Saccharomyces* L-208; *Saccharomyces* L-140; and *Saccharomyces cerevisae* L-169 (hybrid 5-non-flocculant). In some non-limiting embodiments preference may be given to *Saccharomyces cerevisae* strains L-180 and L-181, which are also deposited at the Central Bureau Voor Schimmel Culture, Delft, Holland under the strain numbers CBS 2959 and CBS 1242, respectively.

Fermentation may be carried out over any desired time period in which a desired amount of fermentation-based products are produced. Such may range, in one non-limiting embodiment, from one day to six months. In another non-limiting embodiment, the time period may range from one day to two months.

Those skilled in the art will be aware of appropriate equipment, including tanks, vats, and the like for carrying out the process. Because fermentation of sugar-containing media produces, among its fermentation products, carbon dioxide, it is necessary to ensure that appropriate means for channeling the carbon dioxide away from the sugar-containing medium are provided, to ensure that bursting of the medium container does not occur. One such approach is simply to conduct the fermentation in an open vessel. Other means include, for example, tubing or piping above the surface of the medium, leading to an appropriate outlet.

The organic biocide may be any organic compound having a range of from about 1 to about 20 carbon atoms, in certain non-limiting embodiments from about 5 to about 15 carbon atoms, that is selected from the following list. In certain non-limiting embodiments the biocide is selected from the group consisting of aliphatic and aromatic monoaldehydes and dialdehydes, such as formaldehyde, glutaraldehyde, orthophthalic aldehyde, hexanedial, heptanedial, octanedial, hexanal, heptanal, and octanal. It may be selected from a non-halogenated phenolic, such as o-phenylphenol or one of its corresponding sodium or potassium salts. It may be a compound that releases formaldehyde upon contact with water, such as tetrakis(hydroxymethyl) phosphonium sulphate, an oxazolidine, a triazine, a hydantoin, cis/trans 1-(3-chloro-allyl)-3,5,7-triaza-1-azoniaadamantane chloride, or tris(hydroxymethyl)-nitro-methane. It may be selected from guanidine-based compounds, such as guanidine, biguanides, and polyguanides including, for example, polyhexamethylene biguanide hydrochloride (PHMB). It may be selected from isothiazolinone compounds, such as 5-chloro-2-methyl-4-isothiazolin-3-one, 2-methyl-4-isothia-zolin-3-one, and 2-benzisothiazolin-3-one. It may be 2-bromo-2-nitro-1,3-propanediol ("Bronopol"), 2,2-dibromo-3-nitrilo-propionamide (DBNPA), bromonitrostyrene, or 2,6-dimethyl-m-dioxan-4-ol acetate. It may be a combination of two or more of any of the foregoing.

Commercially-available examples of oxazolidine compounds may further include, for example, DOWICIL™ 96 and BIOBAN™ CS-1135 from The Dow Chemical Company. Examples of triazines may include GROTAN™ from Troy Corporation. A commercially-available example of a hydantoin compound may include Dantogard™ from Lonza. A commercially-available example of cis/trans 1-(3-chloro-allyl)-3,5,7-triaza-1-azoniaadamantane chloride may include DOWICIL™ 75, available from The Dow Chemical Company. A commercially-available example of tris(hydroxymethyl)nitro-methane may include TRIS NITRO™ available from The Dow Chemical Company. Tetrakis(hydroxymethyl) phosphonium sulphate is available as AQUCAR™ THPS 75 from The Dow Chemical Company. The isothiazolinone compounds may include, for example, 5-chloro-2-methyl-4-isothiazolin-3-one with 2-methyl-4-isothiazolin-3-one, available as CANGUARD™ CM, and 2-benzisothiazolin-3-one, available as CANGUARD™ BIT, both from The Dow Chemical Company. Non-halogenated phenolics may include, for example, o-phenylphenol and its corresponding sodium and/or potassium salts, such as DOWICIDE™ manufactured by The Dow Chemical Company. Combinations of any of the additives and/or types of additives listed hereinabove may alternatively be selected.

In a particular non-limiting embodiment the biocide is glutaraldehyde, which has the general formula $C_5H_8O_2$ and the general structure

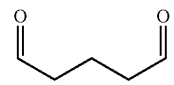

It is also called pentanedial or 1,5-pentanedione and may be obtained from a variety of commercial sources. Those skilled in the art will be aware of the many ways it may be prepared, including, for example, by conversion of a propylene feedstream to a heterodiene acrolein, followed by reaction of the acrolein with a vinyl ether to form 2-methoxy-3,4-dihydro-2H-pyran. The 2-methoxy-3,4-dihydro-2H-pyran may then be hydrolyzed in the presence of a suitable catalyst to produce glutaraldehyde. See, for example, U.S. Pat. No. 6,187,963. Other methods of preparing glutaraldehyde are well known, and those skilled in the art will be easily able to determine appropriate preparation steps. Glutaraldehyde is available commercially in various solution concentrates ranging from 1 percent to 50 percent by weight. Examples of such commercial glutaraldehyde solutions include those which are sold under the UCARCIDE™ tradename by The Dow Chemical Company. Other aromatic and aliphatic monoaldehydes and dialdehydes and formaldehyde-releasing compounds are also commercially available from a variety of sources, including The Dow Chemical Company.

In general, the amount of the additive may range, in certain non-limiting embodiments, from about 10,000 parts per billion (ppb) to about 100 parts per million (ppm), and in other non-limiting embodiments it may range from about 1 ppm to about 100 ppm, based on the total amount of fermentation substrate. In still other non-limiting embodiments the amount may range from about 5 ppm to about 50 ppm, and in yet other non-limiting embodiments it may range from about 10 ppm to about 40 ppm.

The additive may be incorporated at any appropriate point in the process, which is generally performed as a batch operation. In certain non-limiting embodiments the additive is added near or at the beginning of the fermentation process in the fermentation tank, and in other non-limiting embodiments it is added to the must tank. In still other non-limiting embodiments, the additive may be added to both the fermentation tank and the must tank.

Prior to beginning the fermentation procedure, the temperature of the aqueous, sugar-containing medium is, in many embodiments, elevated to within the range of from about 95° C. to about 105° C., that is, to approximately the boiling temperature of the water, for a relatively short period of from about 5 minutes to about 10 minutes. This serves to pasteurize the starting fermentation substrate. The substrate is then cooled, to a temperature most desirably within the range of from about 28° C. to about 35° C., at which temperature an inoculum of the selected fermentation microorganism, i.e., the yeast, is introduced into the aqueous suspension.

The starting proportions of water:sugar:yeast may be varied according to the knowledge of those skilled in the art and optimized in a given production situation on the basis of routine experimentation. However, in one non-limiting embodiment it has been found that a water:sugar:yeast weight proportion of 78:15:7 may be effective. In general, a water:sugar:yeast weight proportion of from about 70:20:10 to about 80:15:5 may be desirable, though use of more or less of each proportion may be effective. Such proportional variations will obviously affect total fermentation time and/or yield under identical conditions. The organic biocide and quaternary ammonium compound combination may be added at any time, but preferably with the addition of the water, sugar and yeast. When the organic biocide is glutaraldehyde, it is preferably added either before the fermentation step and/or during the fermentation step, including simultaneously to the sugar-cane juice and yeast feeding procedure. In the invention, it is not necessary to deactivate the glutaraldehyde before addition of the yeast, and in fact it is an advantage of the invention that the glutaraldehyde can be present throughout the fermentation reaction without detrimental effect on the reaction.

The pH of the suspension may then be adjusted to within a range of about 1.5 to 7, employing, for example, hydrochloric acid or other standard reagent for this purpose, usually contemporaneously with addition of the yeast, in order to provide optimum conditions for effective fermentation. A separate source of inorganic nitrogen may be added in order to increase conversion to ethanol, but such may not be necessary in all methods of production of fermentation products. See, for example, Bose, K. and Ghose, T. K., Process Biochem. 8 (2) 23 (1973), which is incorporated herein by reference in its entirety.

During the fermentation the sugar, for example, sucrose, in the sugar-containing medium will be transformed by the yeast into ethanol and carbon dioxide, on a stoichiometric basis, under anaerobic conditions. This sugar consumption will tend to decrease the bulk concentration of sugar in solution. As fermentation proceeds, the bulk concentration of the ethanol in solution will increase.

Once the fermentation is complete and all the sugar has been converted to ethanol and carbon dioxide, the ethanol may be recovered. Such may be accomplished by any means known to those skilled in the art, for example, by standard filtration and distillation of the ethanol/yeast suspension. The ethanol thus recovered is useful for many industrial and commercial purposes.

The use of the additive may thus enable a production process wherein is experienced reductions in bacterial contamination, interference with yeast viability, yeast flocculation, process infection level (the ratio of total bacteria level to yeast level, an indicator of process efficiency), and need for antibiotics. In fact, the need for antibiotics may, in some non-limiting embodiments, be completely eliminated.

The description and examples discussed hereinabove and below are intended to provide to the skilled practitioner the general concepts, means and methods necessary to understand the invention and, when combined with a level of understanding typical of those skilled in the art, to practice it. It will therefore be understood that not all embodiments deemed to be within the scope of the invention are herein explicitly described, and that many variations of each embodiment, including but not limited to selection of the sugar source, additive compound or combination of compounds, addition point and addition order, fermentation and other processing times, temperatures and other conditions, treatment protocols and equipment, and the like, not described explicitly or in detail herein, will still fall within the general scope of the invention.

The invention having been generally described, the following example is given as a particular embodiment of the invention and to demonstrate the practice and advantages thereof. It is understood that the example is given by way of illustration and is not intended to limit the specification or the claims to follow in any manner. Unless specified otherwise, all amounts here are by weight.

EXAMPLE

Comparative Example 1

A comparison is done to show the effect of the use of three different materials exhibiting biocidal activity on both bacteria and yeast levels level in various media and at various points in time, compared to the effect of adding UCARCIDE™ 250, which is glutaraldehyde. SDA medium is synthetic defined agar, and PCA medium is plate count agar. Dow Antimicrobial™ 7287 is a composition containing 20 percent 2,2-dibromo-3-nitrilopropionamide (DBNPA), sold by The Dow Chemical Company. The results are shown in Table 3.

TABLE 3

| Biocide | Biocide concentration (ppm) | Yeast level[1] (cfu/ml)* | Bacteria level[2] (cfu/ml) | Yeast level[3] (cfu/ml) | Bacteria level[4] (cfu/ml) |
|---|---|---|---|---|---|
| UCARCIDE ™ 250 | 50 | | | $5.0 \times 10^4$ | $5.0 \times 10^5$ |
| Diethyl Carbamate** | 50 | | | $<1.0 \times 10^4$ | $2.6 \times 10^7$ |
| Dow Antimicrobial[5] 7287 ™ | 50 | | | $8.0 \times 10^4$ | $4.0 \times 10^5$ |
| Control** | 0 | $2.0 \times 10^4$ | $8.4 \times 10^7$ | $1.2 \times 10^4$ | $3.3 \times 10^8$ |

*cfu/ml is colony forming units per milliliter
**indicates not an example of the invention
[1]denotes SDA medium
[2]denotes PCA medium
[3]denotes SDA medium, 2 hours after contact
[4]denotes PCA medium, 2 hours after contact
[5]denotes precipitation and color change of the fermentation medium were seen

What is claimed is:

1. A method of producing a fermentation based product comprising fermenting a sugar-containing medium with yeast in the presence of an additive comprising gluteraldehyde in an amount sufficient to reduce or control a bacterial population in the sugar-containing medium;
wherein the amount of the additive ranges from 10,000 ppb to 100 ppm.

2. The method of claim 1 wherein the fermentation-based product is ethanol.

3. The method of claim 1 wherein the sugar-containing medium includes sugar obtained from the group consisting of sugar cane, sugar beets, date palm, sorghum, sugar maple, corn, cellulosic feedstocks, and combinations thereof.

4. The method of claim 1 wherein the additive exhibits a biocidal activity by reducing the bacteria level in the sugar containing medium during the fermentation to a desired level, and wherein the use of other compounds exhibiting the biocidal activity is reduced as compared with an identical sugar-containing medium without the additive.

5. The method of claim 1 wherein no other compound exhibiting the biocidal activity is used.

* * * * *